United States Patent
Krafczyk et al.

(10) Patent No.: US 9,994,596 B2
(45) Date of Patent: Jun. 12, 2018

(54) PROCESS FOR PREPARING A COMPOSITION CONTAINING 2-ETHYLHEXYL SILICATE

(71) Applicant: Evonik Degussa GmbH, Essen (DE)

(72) Inventors: Roland Krafczyk, Rheinfelden (DE); Burkhard Standke, Loerrach (DE); Alexander Koepfer, Zell im Wiesental (DE); Sascha Erhardt, Rheinfelden (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days. days.

(21) Appl. No.: 15/415,401

(22) Filed: Jan. 25, 2017

(65) Prior Publication Data
US 2017/0210763 A1 Jul. 27, 2017

(30) Foreign Application Priority Data
Jan. 26, 2016 (EP) ..................................... 16152742

(51) Int. Cl.
*C07F 7/02* (2006.01)
*C08G 77/08* (2006.01)
*C08G 77/18* (2006.01)

(52) U.S. Cl.
CPC .............. *C07F 7/025* (2013.01); *C08G 77/08* (2013.01); *C08G 77/18* (2013.01)

(58) Field of Classification Search
None
See application file for complete search history.

(56) References Cited

U.S. PATENT DOCUMENTS

| 6,541,552 B1 | 4/2003 | Tsuda et al. |
| 2010/0159144 A1* | 6/2010 | Standke .................. C09D 4/06 427/387 |

FOREIGN PATENT DOCUMENTS

EP  1 035 184 A1  9/2000

OTHER PUBLICATIONS

European Search Report dated Jul. 11, 2016 in Patent Application No. 16152742.9 (with English Translation of Category of Cited Documents).

* cited by examiner

*Primary Examiner* — Clinton A Brooks
(74) *Attorney, Agent, or Firm* — Grüneberg and Myers PLLC

(57) ABSTRACT

A composition containing 2-ethylhexyl silicate, is produced by heating a reaction mixture of ethyl silicate with an excess amount of 2-ethylhexanol in the presence of titanium tetrabutoxide as catalyst to a temperature below the boiling point of 2-ethylhexanol while mixing, allowing the reaction mixture to react and, after the reaction, removing ethanol and excess 2-ethylhexanol from the reaction mixture by distillation and obtaining the composition containing 2-ethylhexyl silicate.

7 Claims, No Drawings

PROCESS FOR PREPARING A COMPOSITION CONTAINING 2-ETHYLHEXYL SILICATE

BACKGROUND OF THE INVENTION

Field of the Invention

The present invention relates to a composition having a very high proportion of 2-ethylhexyl silicate and to a specific process for preparation thereof, wherein ethyl silicate is transesterified with 2-ethylhexanol in the presence of a nonacidic catalyst and then the free alcohol is removed from the reaction mixture.

Discussion of the Background

Alkyl polysilicates, also called alkyl silicates, can be represented according to chemical understanding by general formulae including RO—[(RO—)$_2$Si—O]$_n$—R and [—Si(—OR)$_2$O$_{2/2}$-]$_n$, with n>1 and R=alkyl, and have long been known as such, for example in the form of what is called ethyl silicate.

DE-B 1010739 teaches the preparation of polysilicic esters by reaction of tetraethoxysilane with higher alcohols such as cyclohexanol, methylcyclohexanol and phenols in the presence of an anhydrous or aqueous carboxylic acid as condensing agent, for example acetic or formic acid. The volatile compounds formed in the reaction, such as lower alcohol, were distilled off. The product contains acid.

U.S. Pat. No. 2,846,459 discloses the preparation of brominated alkyl silicates by transesterification, wherein the examples proceeded from ethyl polysilicate and the latter was reacted, inter alia, with a mixture of 2,3-dibromopropan-1-ol and 2-ethylhexanol. Catalysts used here were sodium methoxide or a mixture of sodium methoxide and potassium carbonate. Here too, the compounds that were still volatile after the reaction, such as lower alcohol, were distilled off and hence corresponding brominated alkyl silicates were obtained.

Example 7 of EP1035184A1 discloses the reaction of 100 g of ethyl silicate with 18 g of 2-ethylhexanol in the presence of sulphuric acid as catalyst. The reaction was effected over 1 hour at 120° C. The volatile constituents still present thereafter were distilled off. This afforded an alkyl silicate that still had a content of 94 mol % of ethyl and a molecular weight of 1750 g/mol. Only partial transesterification was effected here with a low yield, and the product, furthermore, is acidic because of the residual amount of sulphuric acid used and remaining in the product. The product was processed further in THF.

SUMMARY OF THE INVENTION

The problem addressed by the present invention was therefore that of providing a composition containing 2-ethylhexyl silicate, including a suitable preparation process, wherein ethyl silicate (ethyl polysilicate) is to be transesterified with 2-ethylhexanol in the presence of a nonacidic catalyst with maximum yield.

The stated problem is advantageously solved by the invention according to the features in the present claims.

Thus, in a surprising manner, a specific process has been found for preparing a composition containing 2-ethylhexyl silicate, by combining ethyl silicate, a relative excess of 2-ethylhexanol based on weight, and a catalytic amount of titanium tetrabutoxide, heating the reactant mixture to a temperature below the boiling point of 2-ethylhexanol while mixing, allowing it to react and, after the reaction, removing ethanol and excess 2-ethylhexanol from the reaction mixture/product mixture thus obtained by distillation, and obtaining the composition of the invention as the bottom product in excellent yield after distillation. Furthermore, the composition of the invention is nonacidic and advantageously contains a 2-ethylhexyl silicate content of ≥90% by weight and a free ethanol content of ≤1% by weight, based in each case on the composition.

DETAILED DESCRIPTION OF THE INVENTION

The present invention thus provides a process for preparing a composition containing 2-ethylhexyl silicate, by heating ethyl silicate with an amount of 2-ethylhexanol used in excess in the presence of titanium tetrabutoxide as catalyst to a temperature below the boiling point of 2-ethylhexanol while mixing, allowing them to react and, after the reaction, removing ethanol and excess 2-ethylhexanol from the reaction mixture by distillation and obtaining the product.

Advantageously, in the process according to the invention, ethyl silicate and 2-ethylhexanol are used in a weight ratio of 1:1.1 to 10, preferably 1:1.5 to 3, more preferably 1:2.

Moreover, in the process according to the invention, advantageously 0.01% to 0.5% by weight, preferably from 0.01% to 0.1% by weight and more preferably 0.05% by weight of titanium tetrabutoxide, based on the amount of 2-ethylhexyl silicate used, is used.

Suitably, in the process according to the invention, the reaction is conducted at a temperature of 140 to 182° C., preferably of 170 to 181° C., more preferably at 180° C., and over a period of 12 to 60 hours, preferably of 16 to 48 hours.

In general, the process according to the invention is conducted as follows:

In general, a mixture of ethyl silicate and a relative excess of 2-ethylhexanol in terms of weight, and also a catalytic amount of titanium tetrabutoxide, is initially charged in a suitable reaction apparatus (for example reaction vessel with feeds for reactant metering, stirrer, heating, temperature control/regulation, reflux condenser and bridge with receiver), the mixture is heated while stirring, preferably to a temperature just below the boiling point of 2-ethylhexanol, especially at a temperature in the region of 180° C., the mixture is allowed to react for a sufficiently long period, preferably of 12 to 48 hours, and then the volatile components still present in the reaction mixture/product mixture thus obtained, such as ethanol and excess 2-ethylhexanol are suitably distilled, in order to work up the reaction mixture/product mixture by means of distillation and hence obtain the product. For example, for performance of the distillation, the reaction mixture/product mixture present after a reaction can be transferred from the reaction vessel into a separate distillation unit and be worked up by means of distillation. In addition, it is possible to apply vacuum toward the end of the distillation, i.e. to distill under reduced pressure, and/or additionally to pass nitrogen through the product/product mixture present in the bottom of the distillation apparatus. The product, the composition according to the invention, is thus advantageously obtained as a colourless to yellowish, slightly viscous liquid in the bottom of the distillation apparatus used.

Surprisingly, the performance of the process according to the invention, in a particularly advantageous manner, achieves virtually complete transesterification with a yield of ≥95% and hence favourably makes it possible to provide a corresponding reaction product and, by the process according to the invention, advantageously makes it possible to obtain a composition having a high 2-ethylhexyl silicate content of ≥90% by weight, preferably ≥95% by weight.

The present invention therefore also provides compositions having a 2-ethylhexyl silicate content of ≥90% by weight, preferably ≥95% by weight, obtainable by the process according to the invention.

The invention further provides a composition or composition prepared in accordance with the invention having a 2-ethylhexyl silicate content of ≥90% by weight, preferably ≥95% by weight, based on the composition. In addition, a composition according to the invention or composition prepared in accordance with the invention preferably has an ethanol content of ≤1% by weight, preferably ≤0.5% by weight down to the detection limit, based on the composition, and is thus also notable from an environmental point of view additionally for a very low proportion of VOCs (volatile organic compounds).

It is thus advantageously possible to use compositions according to the invention, for example—but not exclusively—as coupling reagent in the preparation of functional polymers, such as butadiene rubber, or in solution styrene-butadiene rubber.

The present invention is elucidated in detail by the examples which follow, without restricting the subject-matter of the invention:

Having generally described this invention, a further understanding can be obtained by reference to certain specific examples which are provided herein for purposes of illustration only, and are not intended to be limiting unless otherwise specified.

EXAMPLES

Chemicals Used:
Dynasylan® 40 (ethyl silicate), Evonik Resource Efficiency GmbH
Titanium tetrabutoxide, Sigma-Aldrich
2-Ethylhexanol, Sigma-Aldrich
Analytical Methods:
NMR Measurements:
Instrument: Bruker
Frequency: 100.6 MHz ($^{13}$C-NMR)
Scans: 1024 ($^{13}$C-NMR)
Temperature: 296 K
Solvent: $CDCl_3$
Standard: tetramethylsilane
Gas Chromatography Determination of Alcohol:

All figures should be understood as guide values. Columns of similar polarity, for example from other manufacturers, are permitted. If the separation is demonstrably also achievable with an instrument having a packed column, this is also permitted.

In the handling of the samples, the moisture sensitivity thereof should be noted.

Instrument: Capillary gas chromatograph with TCD and integrator e.g. HP 5890 with HP 3396 integrator
Separation column: Capillary column
Length: 25 m
Internal diameter: 0.20 mm
Film thickness: 0.33 mm
Stationary phase: HP Ultra 1
Temperatures: Column oven: 120° C.—2 min—10°/min—275° C.—8 min
Injector: 250° C.
Detector: 280° C.
Carrier gas: helium
Flow rate: about 1 ml/min
Split ratio: about 1:100
Sample injected: 0.4 ml
Evaluation is effected by standardization to 100 area %.

Example 1

Dynasylan® 40 (50 g), 2-ethylhexanol (100 g) and titanium tetrabutoxide (25 μl, 0.05% by weight, based on the amount of Dynasylan® 40 used) were initially charged and heated to 180° C. while stirring. Ethanol formed was removed from the reaction mixture by means of a distillation system. The mixture was stirred at this temperature for 24 h, then 2-ethylhexanol (b.p. 182° C.) was distilled off at atmospheric pressure. The residual free alcohol was removed under reduced pressure (1 mbar, 100° C.). The reaction product obtained (105 g) was a pale yellowish, slightly viscous liquid. The reaction product was analysed by means of $^{13}$C NMR. The analysis demonstrates that the reaction product obtained was a 2-ethylhexyl silicate. The transesterification yield was ≥95%, i.e. ≥95% of the ethoxy groups of the ethyl silicate used were replaced by 2-ethylhexyloxy groups, i.e. transesterified, in accordance with the invention.

$^{13}$C-NMR (100 MHz, $CDCl_3$): δ=65.2-66.0 (m, 1C), 41.2-41.8 (m, 1C), 29.7-30.2 (m, 1C), 28.9-29.3 (br s, 1C), 22.7-23-5 (m, 2Cs), 13.9-14.3 (s, 1C), 10.8-11.2 (m, 1C) ppm.

European patent application 16152742.9 filed Jan. 26, 2016, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A process for preparing a composition containing, 2-ethylhexyl silicate, said process comprising:
heating a reaction mixture of ethyl silicate with an excess amount of 2-ethylhexanol in the presence of titanium tetrabutoxide as catalyst to a temperature below the boiling point of 2-ethylhexanol while mixing,
allowing the reaction mixture to react and,
after the reaction, removing ethanol and excess 2-ethylhexanol from the reaction mixture by distillation and obtaining the composition containing 2-ethylhexyl silicate.

2. The process according to claim 1,
wherein the weight ratio of ethyl silicate and 2-ethylhexanol is 1:1.1 to 1:10.

3. The process according to claim 1,
wherein the amount of titanium tetrabutoxide is 0.01% to 0.5% by weight, based on the amount of 2-ethylhexyl silicate used.

4. The process according to claim 1,
wherein the reaction is conducted at a temperature of 140 to 182° C.

5. The process according to claim 1,
wherein the reaction is conducted over a period of 12 to 60 hours.

6. The process according to claim 1,
wherein the transesterification reaction is conducted with a yield of ≥95%.

7. The process according to claim 1,
wherein said composition comprises a 2-ethylhexyl silicate content of ≥90% by weight.

* * * * *